US009482646B2

(12) United States Patent
Nagae et al.

(10) Patent No.: US 9,482,646 B2
(45) Date of Patent: Nov. 1, 2016

(54) OBJECT INFORMATION ACQUIRING APPARATUS

(71) Applicant: CANON KABUSHIKI KAISHA, Tokyo (JP)

(72) Inventors: Kenichi Nagae, Yokohama (JP); Kengo Kondo, Kyoto (JP); Makoto Yamakawa, Kyoto (JP); Tsuyoshi Shiina, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 101 days.

(21) Appl. No.: 14/355,262

(22) PCT Filed: Nov. 2, 2012

(86) PCT No.: PCT/JP2012/079047
§ 371 (c)(1),
(2) Date: Apr. 30, 2014

(87) PCT Pub. No.: WO2013/069752
PCT Pub. Date: May 16, 2013

(65) Prior Publication Data
US 2014/0245836 A1 Sep. 4, 2014

(30) Foreign Application Priority Data
Nov. 7, 2011 (JP) .................. 2011-243483

(51) Int. Cl.
*G01N 29/36* (2006.01)
*A61B 5/00* (2006.01)
(Continued)

(52) U.S. Cl.
CPC ............. *G01N 29/36* (2013.01); *A61B 8/485* (2013.01); *A61B 8/5207* (2013.01); *G01N 29/34* (2013.01);
(Continued)

(58) Field of Classification Search
CPC .... A61B 8/485; A61B 8/5207; G01N 29/34; G01N 29/36; G01N 29/44
See application file for complete search history.

(56) References Cited

U.S. PATENT DOCUMENTS

| 6,048,315 A | 4/2000 | Chiao et al. .................. 600/447 |
| 2002/0008692 A1* | 1/2002 | Omura ..................... G06F 1/16 345/173 |

(Continued)

FOREIGN PATENT DOCUMENTS

| EP | 2356941 | 8/2011 |
| WO | WO 2010/053156 A | 5/2010 |
| WO | WO 2010/102302 A2 | 9/2010 |

OTHER PUBLICATIONS

Office Action issued Dec. 1, 2015 in counterpart Japanese patent application 2011-243483, with translation.

*Primary Examiner* — Baisakhi Roy
(74) *Attorney, Agent, or Firm* — Fitzpatrick, Cella, Harper & Scinto

(57) ABSTRACT

Disclosed is an apparatus that transmits an elastic wave to an object and receives a reflected wave, this apparatus including: a transmitting and receiving unit having elements for converting an elastic wave to an electric signal, and being arranged at least in one direction; an element controlling unit that inputs an electric signal to the element and causes the element to transmit an elastic wave; and a detecting unit that detects a reflected wave to be received by the element, wherein the electric signal to be inputted to the element is an encoded pulse signal encoded among the elements, and the detecting unit decodes the reflected wave and executes at different time points aperture synthesis processing of synthesizing the decoded reflected wave with respect to the intersections of two axes at different time points.

6 Claims, 7 Drawing Sheets

(51) Int. Cl.
  *A61B 8/08* (2006.01)
  *G01S 15/89* (2006.01)
  *G01S 7/52* (2006.01)
  *G01N 29/34* (2006.01)
  *G01N 29/44* (2006.01)

(52) U.S. Cl.
  CPC ........... *G01N 29/44* (2013.01); *G01S 7/52042* (2013.01); *G01S 15/8959* (2013.01); *G01S 15/8977* (2013.01); *G01S 7/5209* (2013.01); *G01S 7/52085* (2013.01)

(56) References Cited

U.S. PATENT DOCUMENTS

| | | | | |
|---|---|---|---|---|
| 2006/0173334 A1* | 8/2006 | Azuma | ................... | A61B 8/00 600/447 |
| 2006/0241429 A1* | 10/2006 | Ustuner | ............... | G10K 11/346 600/437 |
| 2007/0239002 A1 | 10/2007 | Alam | ........................... | 600/437 |
| 2008/0028855 A1* | 2/2008 | Kano | .................. | G01C 19/5698 73/504.12 |
| 2008/0253229 A1* | 10/2008 | Liu | ...................... | G01N 29/041 367/87 |
| 2010/0094561 A1* | 4/2010 | Masumura | ........... | A61B 5/0073 702/19 |
| 2010/0223999 A1* | 9/2010 | Onoe | ....................... | H03H 3/08 73/579 |
| 2010/0286516 A1 | 11/2010 | Fan et al. | ...................... | 600/438 |
| 2011/0071335 A1* | 3/2011 | Ueda | ........................ | A61N 2/02 600/12 |
| 2011/0083511 A1 | 4/2011 | Taki et al. | ........................ | 73/602 |
| 2011/0270088 A1* | 11/2011 | Shiina | ....................... | A61B 8/08 600/443 |
| 2011/0307181 A1 | 12/2011 | Nagae | ............................. | 702/19 |
| 2012/0314534 A1 | 12/2012 | Yoda et al. | ..................... | 367/7 |
| 2013/0338944 A1 | 12/2013 | Nagae et al. | .................... | 702/56 |
| 2014/0056105 A1 | 2/2014 | Nagae et al. | .................... | 367/87 |
| 2014/0206960 A1 | 7/2014 | Nagae | ............................. | 600/310 |

* cited by examiner

301 — 304
302 — 303

OBJECT INFORMATION ACQUIRING APPARATUS

TECHNICAL FIELD

The present invention relates to an object information acquiring apparatus using an ultrasound wave.

BACKGROUND ART

Generally an ultrasound diagnostic apparatus not only displays an ultrasonographic image (a B-mode image) which visualizes a structure inside a bio-tissue based on a reflected wave that shows acoustic impedance distribution in tissue, but also has a function to visualize the blood flow and motion of tissues.

Also recently estimating the hardness of a tissue portion in use of ultrasound waves has begun, and data thus obtained is used for diagnosing tissue. A strain inside the tissue, generated by such a method as applying static pressure from the surface of the body or applying excitation using a relatively low frequency ultrasound waves, is measured using ultrasound waves, and hardness of the tissue is estimated based on the amount of the strain. To calculate this strain, the displacement distribution of each point, measured with the ultrasound waves, is divided by a distance between each point.

Upon calculating the motion of a tissue or hardness of a tissue portion like this, displacement measured with ultrasound waves is frequently used, and therefore in recent ultrasound diagnostic apparatuses, a critical technical issue is the displacement measurement using ultrasound waves.

Patent Literature 1 (PTL 1) discloses an ultrasound diagnostic apparatus that measures displacement using an echo signal string effectively focused on sampling points arranged on a hyperbola-ellipse. PTL 1 also discloses a technique for setting a virtual wave source and performing transmission using a plurality of elements in order to improve the SN ratio in the case of using an aperture synthesis method for effectively focusing the echo signals on sampling points arranged on a hyperbola-ellipse.

CITATION LIST

Patent Literature

PTL 1: PCT Application Publication No. 2010/053156

SUMMARY OF INVENTION

Technical Problem

However in the case of setting a virtual wave source and performing transmission using a plurality of elements to measure displacement, the transmission conditions are sometimes not optimum for the aperture synthesis method.

In the case of using the aperture synthesis method, the spatial resolution improves as the transmitting wave is close to a spherical wave. It is preferable that observation is possible in a direction of which angle is wider from a direction perpendicular to the plane where elements of an ultrasound wave transmitting and receiving unit (probe) are arranged, and for example, a cylindrical wave front is formed to visualize a two-dimensional cross-section. In other words, if the aperture synthesis method is used for an ultrasound diagnostic apparatus, an optimum transmission method uses only one element for transmission, as long as a drop in the SN ratio is of no concern.

In the case of transmission using the virtual wave source, however, a plurality of elements are used for transmission, hence it is difficult to generate an ideal spherical wave or a cylindrical wave front, compared with the case of using one element for transmission. Therefore limitation is inevitable to implement both maintaining a high SN ratio and optimum transmission conditions for the aperture synthesis method.

With the foregoing in view, it is an object of the present invention to improve accuracy upon using the aperture synthesis method in order to measure displacement using ultrasound waves in the object information acquiring apparatus.

Solution to Problem

To solve this problem, the present invention provides an object information acquiring apparatus that transmits an elastic wave to an object and receives a reflected wave, which is the transmitted elastic wave reflected in the object, so as to acquire information on the object, the apparatus comprising:

a transmitting and receiving unit having a plurality of elements which can perform conversion between an elastic wave and an electric signal, with these elements being arranged at least in one direction;

an element controlling unit that inputs an electric signal to the element and causes the element to transmit an elastic wave to the object; and a detecting unit that detects the reflected wave, which is the transmitted elastic wave reflected in the object and received by the element, wherein the electric signal which the element controlling unit inputs to the element is an encoded pulse signal encoded among the plurality of elements, and the detecting unit decodes the reflected wave and executes an aperture synthesis processing at different time points, by setting as axes a direction along a hyperbola of which focal points are two locations in the one direction in which the plurality of elements are arranged and a direction along an ellipse of which focal points are these two locations, and synthesizing the decoded reflected wave in the intersections of these axes or in locations corresponding to the intersections, and acquires displacement values of the object at least in two directions based on the aperture synthesis processing results at the different time points.

The present invention also provides an object information acquiring apparatus that transmits an elastic wave to an object and receives a reflected wave, which is the transmitted elastic wave reflected in the object, so as to acquire information on the object, the apparatus comprising:

a transmitting and receiving unit in which a plurality of elements, which can perform conversion between an elastic wave and an electric signal, are arranged;

an element controlling unit that inputs an electric signal to the element and causes the element to transmit an elastic wave to the object; and a detecting unit that detects the reflected wave, which is the transmitted elastic wave reflected in the object and received by the element, wherein the electric signal which the element controlling unit inputs to the element is an encoded pulse signal encoded among the plurality of elements, and the detecting unit decodes the reflected wave and executes an aperture synthesis processing for synthesizing the decoded reflected waves at different time points, and acquires displacement values of the object at least in two directions based on aperture synthesis processing results at the different time points.

Advantageous Effects of Invention

According to the present invention, the accuracy is improved upon adopting the aperture synthesis method in order to measure a displacement in use of ultrasound waves in the object information acquiring apparatus is adopted.

Further features of the present invention will become apparent from the following description of exemplary embodiments with reference to the attached drawings.

DESCRIPTION OF EMBODIMENTS

Embodiments of the present invention will now be described with reference to the drawings. The following dimensions, materials and shapes of components and the relative positions thereof should be appropriately changed according to the configuration and various conditions of the apparatus to which the present invention is applied, and are not intended to limit the scope of the present invention.

In the following description, an ultrasound diagnostic apparatus will be described as an example of an object information acquiring apparatus of the present invention. The ultrasound diagnostic apparatus of the present invention is an apparatus utilizing an ultrasound echo technology that transmits an ultrasound wave to an object, and receives an ultrasound wave (echo wave) reflected inside the object so as to acquire the object information as image data. The objects that can be observed are, for example, a part of bio-tissue of a human or animal, and a material simulating a bio-tissue. The object information to be acquired is information reflecting the difference of acoustic impedance in the tissue inside the object. The ultrasound wave in the present invention is a type of elastic wave, and is also called a sound wave, ultrasound wave or an acoustic wave.

<Embodiment 1>

Figure 1:
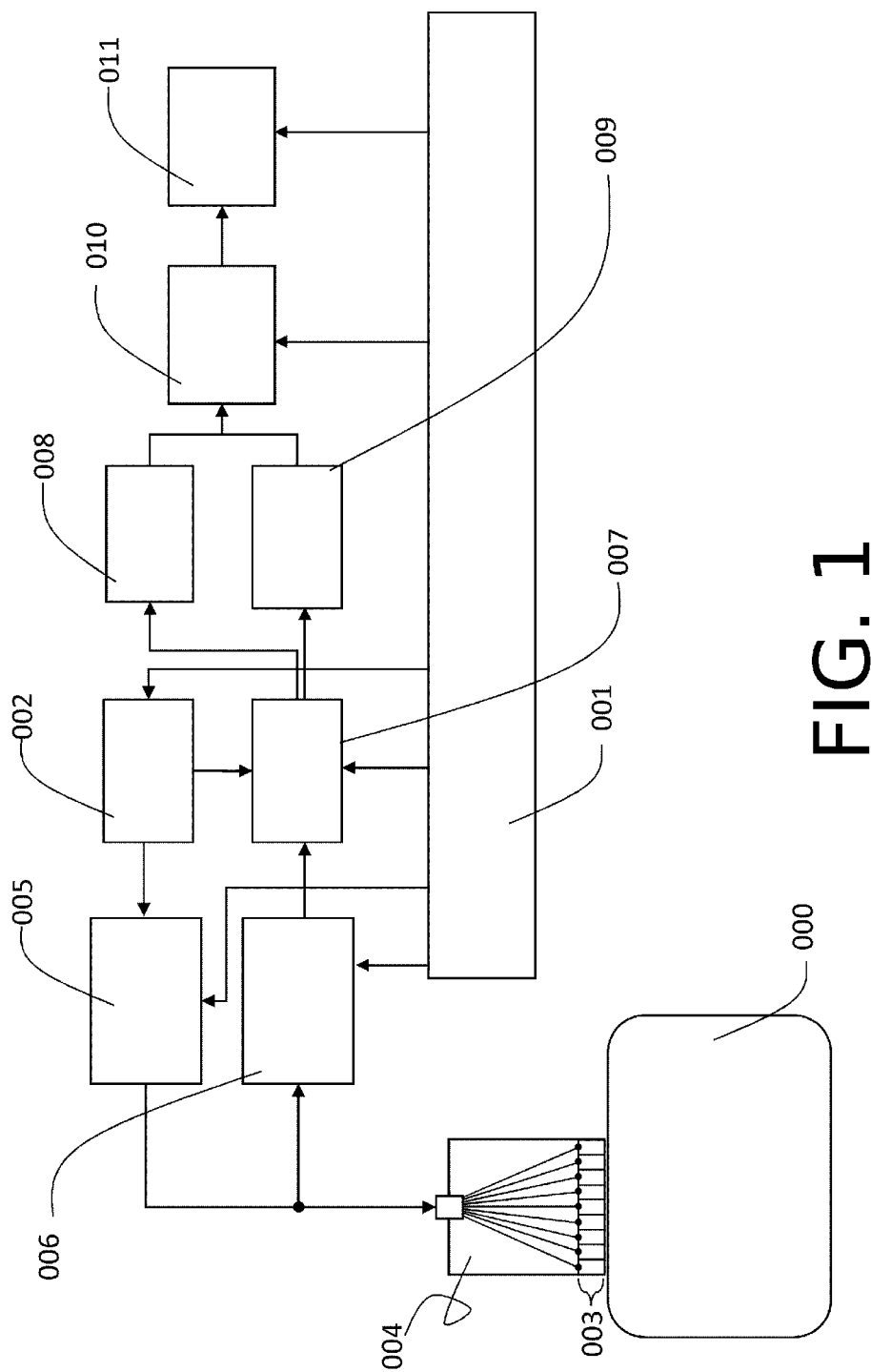
FIG. 1 is a diagram depicting an overview of a system of an object information acquiring apparatus.

FIG. 1 is a diagram depicting an overview of a system of an object information acquiring apparatus according to the present invention. A flow of signals and a role of each block in the apparatus of the present invention will be described with reference to FIG. 1, then the respective processing will be described in detail.

(Overview of System and Flow of Signals)

A code control block 002 generates a code string signal and inputs the code string signal to a transmitting circuit system 005 according to a control signal from a system control unit 001. The transmitting circuit system 005 generates an electric signal having a voltage waveform according to the inputted code string signal. This voltage waveform is converted into an ultrasound wave (elastic wave) by a plurality of ultrasound conversion elements 003, and is transmitted from a probe (transmitting and receiving unit) 004 into an object 000. In the case of ultrasound wave transmission, the system control unit corresponds to an element controlling unit of the present invention.

The ultrasound wave reflected inside the object 000 (reflected wave) is detected by a plurality of ultrasound conversion elements 003, and is converted into a plurality of voltage signals (electric signals), which are inputted into a receiving circuit system 006 as received signals. The ultrasound conversion element can be any element provided that conversion between an ultrasound wave (elastic wave) and an electric signal is possible. In order to perform apodization processing, in the transmitting and receiving unit of ultrasound waves according to the present invention, a plurality of the above mentioned ultrasound conversion elements are arranged in (along) at least one direction.

The receiving circuit system 006 amplifies a plurality of voltage signals and converts the amplified voltage signals into a plurality of digital signals. The digital signals outputted from the receiving circuit system 006 are inputted into a decoding/synthesizing block 007.

The encoding/synthesizing block 007 performs decoding processing and aperture synthesis processing using the inputted plurality of digital signals, information on the code string signal inputted from the code control block 002, and position information and modulation information which are inputted from the system control unit. The decoding/synthesizing block 007 outputs the result of the later mentioned normal apodization to an image generation block 008 as a first aperture synthesis signal, and outputs the result of the modulation apodization to a displacement calculation block 009 as a second aperture synthesis signal.

The image generation block 008 calculates an envelope curve based on the inputted first aperture synthesis signal, and outputs the result to an information processing block 010 as envelope data. The image generation block 008 may perform various processes if necessary, such as filtering the inputted first aperture synthesis signal with a bandpass filter.

The displacement calculation block 009 calculates a displacement, using the plurality of second aperture synthesis signals, which was calculated in use of receive signals acquired at different time points, and outputs the calculated displacement to the image processing block 010 as displacement information data. The decoding/synthesizing block and the displacement calculation block correspond to the detecting unit according to the present invention.

The image processing block 010 performs the intensity adjustment and various filter processes for the inputted envelope data, and outputs impedance brightness data (that is, B-mode image) to an image display system 011 as distribution information reflecting the difference of acoustic impedance of the tissue. The image processing block 010 outputs the inputted displacement information data to the image display system 011 as displacement information brightness data.

The image display system 011 displays the inputted displacement information brightness data and the impedance brightness data according to an instruction from the system control unit 001. For the display method, the displacement information brightness data and the impedance brightness data may be superposed, or may be displayed side by side. Needless to say, it is also possible for only one of the brightness data to be displayed. The display mode can be changed according to an instruction from the system control unit 001.

The displacement calculation block 009 not only calculates displacement, but can also calculate a strain distribution using the calculated displacement, and may output the strain distribution to the image processing block 010 as strain information data, and may also display this data on the image display system 011.

The above is the basic configuration of the object information acquiring apparatus and a flow of signals thereof.

(Ultrasound Wave Transmission Controlled by Code String Signal)

Now operation of the code control block 002 and the transmitting circuit system 005 will be described.

Figure 2:
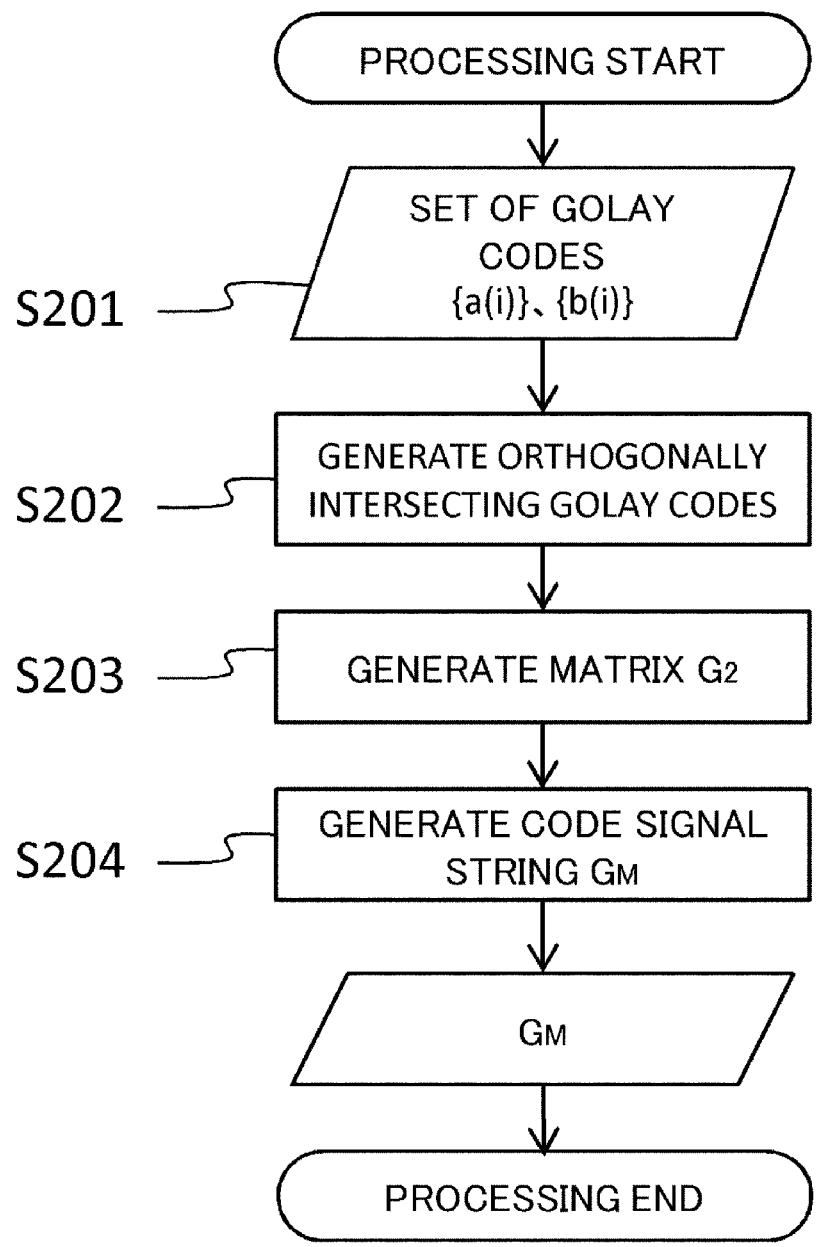
FIG. 2 is a flow chart depicting processing to generate a code string signal.

The code control block 002 generates a code string signal suitable for the number of elements to be used for transmission. Generation of the code string signal will be described with reference to the flow chart in FIG. 2.

First sets of Golay codes $\{a_N(i)\}$ and $\{b_N(i)\}$ ($i=1, \ldots, 2^N$) are prepared (step S201). Each set of the Golay codes is a set of a code string in which the auto correlation value Aj or Bj of $a_N(i)$ or $b_N(i)$ satisfies the following Expression (1) and Expression (2), and $2^N$ indicates a length of the code string.

[Math. 1]

$$A_j = \sum_{i=1}^{2^N-j} a_i a_{i+j}, B_j = \sum_{i=1}^{2^N-j} b_i b_{i+j} \quad (j=0, \ldots, 2^N) \quad (1)$$

$$A_j + B_j = \begin{cases} 2 \times 2^N & (j=0) \\ 0 & (j \neq 0) \end{cases} \quad (2)$$

Then a set of Golay codes that intersects orthogonally with these code strings is generated as Expression (3) (step S202). This is a combination of elements given by Expression (4).

[Math. 2]

$$\{\overline{a}_N(i)\}, \{\overline{b}_N(i)\} (i=1, \ldots, 2^N) \quad (3)$$

$$\overline{a}_N(i) = b_N(-i), \overline{b}_N(i) = -a_N(-i) \quad (4)$$

Here a matrix $G_2$ given by Expression (5), configured by Golay codes which are orthogonal to each other, is created (step S203).

[Math. 3]

$$G_2 = \begin{bmatrix} a_N & b_N \\ \overline{a}_N & \overline{b}_N \end{bmatrix} \quad (5)$$

A code string signal $G_M$ is generated using Expression (6), by determining a Kronecker product with a Hadamard matrix, so that the result becomes the required number of combinations of codes (step S204).

[Math. 4]

$$G_M = G_M \otimes H_{M/2} \quad (6)$$

The Hadamard matrix can be calculated by the following Expression (7) and Expression (8).

[Math. 5]

$$H_1 = [1] \quad (7)$$

$$H_{2k} = \begin{bmatrix} H_k & H_k \\ H_k & -H_k \end{bmatrix} \quad (8)$$

For example, operation when the code string signal is used for four elements will be described with reference to FIG. 3. FIG. 3 schematically shows a voltage waveform of a signal inputted to each element.

The code control block 002 generates a code string signal ($G_4$ in this case) given by Expression (9) using the above mentioned technique. $G_4$ is a code string signal when N=0. The code string signal corresponds to the encoded pulse signal.

[Math. 6]

$$G_4 = \begin{bmatrix} 1 & 1 & 1 & 1 \\ 1 & -1 & 1 & -1 \\ 1 & 1 & -1 & -1 \\ 1 & -1 & -1 & 1 \end{bmatrix} \quad (9)$$

The code string signal is inputted from the code control block 002 to the transmitting circuit system 005. The transmitting circuit system 005 transmits a voltage waveform, corresponding to each column of the code string signal, to the four elements: element 301, element 302, element 303 and element 304.

Figure 3A:
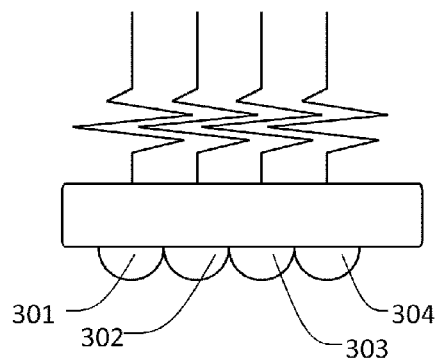
FIGS. 3A to 3D show an operation of elements caused by a code string signal.

First the transmitting circuit system 005 transmits a voltage waveform to each element in a same phase (this phase is assumed to be 0°, for example), using (1, 1, 1, 1) which are arranged in the first column of the code string signal (FIG. 3A).

Figure 3C:
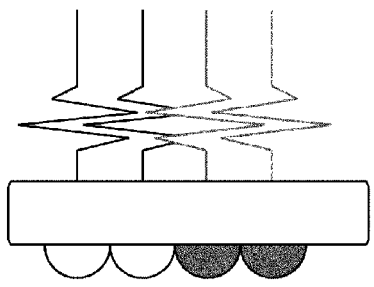
Figure 3B:
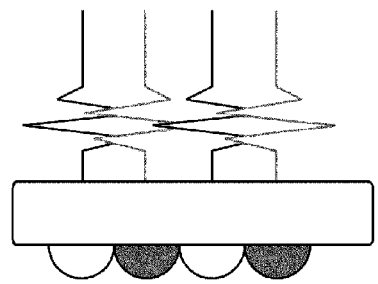

Then the transmitting circuit system 005 transmits a voltage waveform to the element 301 at phase 0°, to the element 302 in phase 180°, to the element 303 in phase 0°, and to the element 304 in phase 180° according to (1, −1, 1, −1) which are arranged in the second column of the code string signal (FIG. 3B).

Then the transmission circuit system 005 transmits a voltage waveform to the element 301 in phase 0°, to the element 302 in phase 0°, to the element 303 in phase 180°, and to the element 304 in phase 180° according to (1, 1, −1, −1) which are arranged in the third column of the code string signal (FIG. 3C).

Figure 3D:
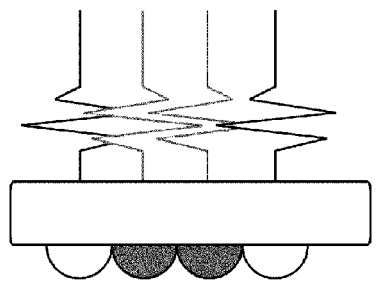

Finally the transmitting circuit system 005 transmits a voltage waveform to the element 301 in phase 0°, to the element 302 in phase 180°, to the element 303 in phase 180°, and to the element 304 in phase 0° according to (1, −1, −1, 1) which are arranged in the fourth column of the code string signal (FIG. 3D).

In FIG. 3, a black element indicates that a voltage waveform in phase 180° is being input. In each transmission, a reflected wave, that is the ultrasound wave reflected inside the object, is generated, is received by the ultrasound conversion element 003, and is converted into an analog electric signal (receive signal).

(Receive Signal Decoding Processing)

Now the receiving circuit system 006 and the decoding/synthesizing block 007 will be described.

The receiving control system 006 amplifies the voltage signals received by the plurality of ultrasound conversion elements 003 in each transmission, and converts the amplified voltage signals into a plurality of digital signals. The digital signals outputted from the receiving circuit system 006 are input into the decoding/synthesizing block 007.

Figure 4:
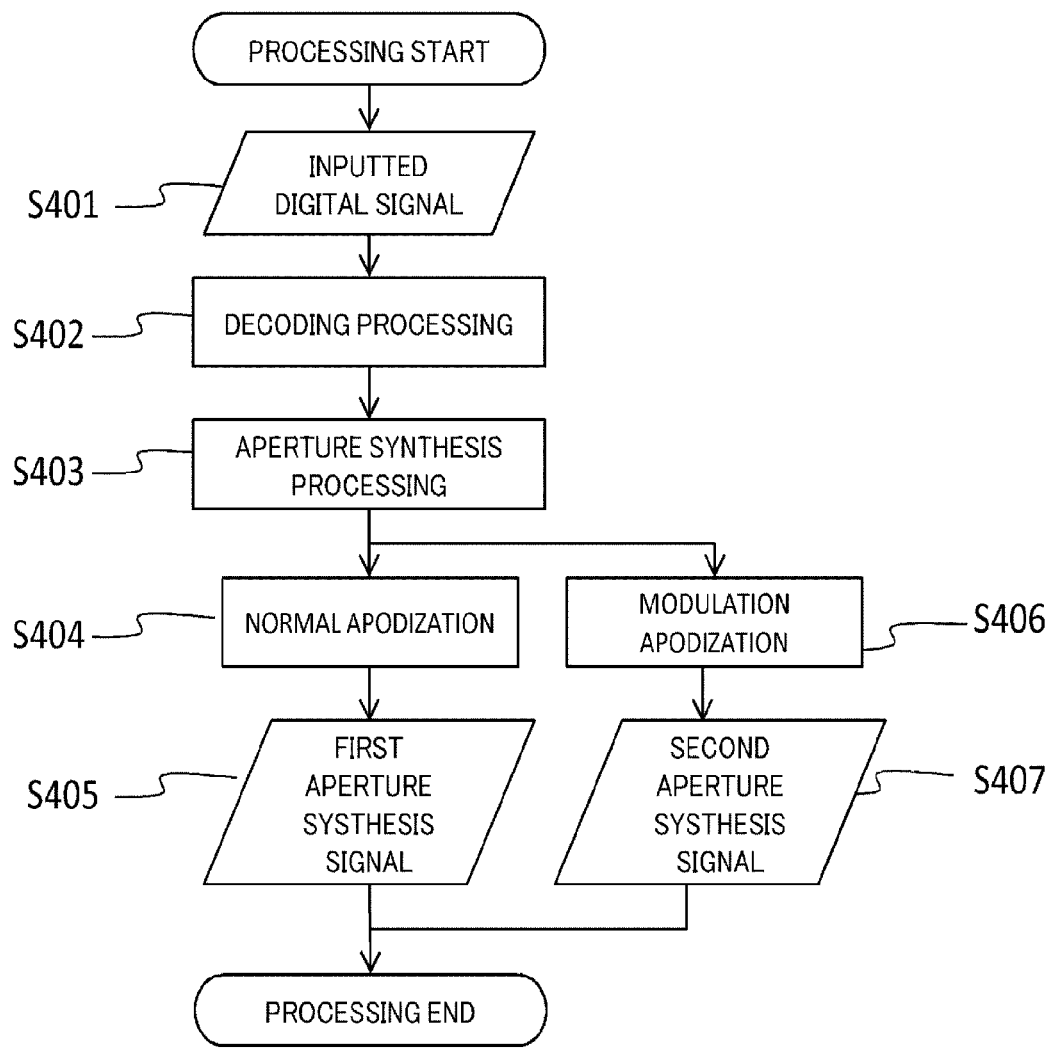
FIG. 4 is a flow chart depicting processing on a received signal.

The operation of the decoding/synthesizing block 007 will be described with reference to FIG. 4.

The decoding/synthesizing block 007 stores a plurality of inputted digital signals in a memory (step S401). When a predetermined number of times of transmission ends, the decoding/synthesizing block 007 executes the decoding processing (step S402).

A signal $R_{Tx,Rx}(t)$ in Expression (10) decoded here is a digital signal which was transmitted by a Tx-th element, and was received by an Rx-th element. In this case, $g_{ij}$ is an element (i, j) of the code string signal, and $r_{ij}(t)$ is a digital signal received when the i-th element executes the j-th transmission.

[Math. 7]

$$R_{Tx,Rx}(t) = \sum_{j=1}^{2^N} (g_{Tx,j} \times r_{Rx,j}) \quad (10)$$

Now the decoding processing will be described in more detail using transmission of the above mentioned four elements as an example.

$r_{ij}(t)$ is a digital signal generated by a receive waveform, which is an ultrasound wave transmitted four times using the code string signal, reflected inside the object and returned. Here i denotes an element which received the digital signal (i=1 is the element 301, i=2 is the element 302, i=3 is the element 303, and i=4 is the element 304), and j denotes the number of times of transmission when this receive signal was transmitted (in this case, j=1, 2, 3, 4). For the plurality of digital signals $r_{ij}(t)$, decoding is performed using the code string signal G4.

For example, a signal $R_{1,1}(t)$, which was transmitted via the first element (element 301) using (1, 1, 1, 1) arranged in the first row of the code string signal and received by the first element (element 301), is given by Expression (11).

[Math. 8]

$$R_{1,1}(t) = 1 \times r_{1,1} + 1 \times r_{1,2} + 1 \times r_{1,3} + 1 \times r_{1,4} \quad (11)$$

At this time, the received wave form of a wave which was transmitted from the second element (element 302), reflected in the object, and returned to the second element (element 302), becomes as follows. An ultrasound wave is transmitted from the second element according to (1, −1, 1, −1). If this is decoded using the above mentioned (1, 1, 1, 1), then 1×1+1×(−1)+1×1+1×(−1)=0, that is, the transmitted ultrasound wave becomes 0 by decoding. In the same manner, an ultrasound wave transmitted from the third element and an ultrasound wave transmitted from the fourth element also become 0 by decoding.

In other words, only the reflected wave of the ultrasound wave transmitted from the first element can be extracted by performing decoding using the code string signal as mentioned above.

The processing result thus far will be summarized. By transmitting ultrasound waves simultaneously from the four elements according to the code string signal and decoding the received waveforms, only the reflected wave of the ultrasound wave transmitted from each element is extracted. This means that the reflected wave is separated after the reception by using a signal encoded among the plurality of elements. As a result of decoding, signals (sixteen types in this example), transmitted from each element and received by all the elements, can be acquired individually. Furthermore, because of the decoding, the same SN ratio as the case of repeating transmission and reception four times is acquired. In other words, if transmission is performed from one element at a time, a total of sixteen times of transmission must be executed to implement an equivalent SN ratio for all the elements, but the present invention implements the SN ratio by four times of transmission.

As a consequence, according to the present invention, a signal equivalent to the case of transmitting one element at a time, that is suitable for the aperture synthesis method, can be acquired with a higher SN ratio via the same number of times of transmission.

Here the code string signal with N=0 was described as an example, but N can be any positive integer, and in this case, the SN ratio can further improve.

(Aperture Synthesis Processing)

Description of the operation of the decoding/synthesizing block 007 continues.

The aperture synthesis processing is performed using the decoded signal $R_{Tx,Rx}(t)$ acquired by the decoding (step S403). In the aperture synthesis processing, sampling points are the intersections of a hyperbola group and an ellipse group of which focal points are shared in two locations. In other words, a direction along a hyperbola of which focal points are two locations in one direction in which the ultrasound conversion elements are arranged, and a direction along an ellipse having the same focal points are set as the X and Y axes, and the intersections of the axes are regarded as the sampling points. Then data where these intersections are focused for transmission and reception is synthesized.

Here the hyperbola group is a set of curves or straight lines selected such that a difference of traveling times of ultrasound pulses from the two focal points become substantially the same. Between adjacent curves or straight lines in the hyperbola group, the value of traveling time difference between ultrasound pulses from the two focal points is different by 1/m of the wavelength of the ultrasound waves in use. The ellipse group is a set of curves selected such that a sum of traveling times of ultrasound pulses from the two focal points becomes substantially the same. Between the adjacent curves in the ellipse group, the value of the sum of the traveling times of the ultrasound pulses from the two focal points is different by 1/n of the wavelength of the ultrasound waves in use. m and n are integers respectively, which preferably is four or more in order to improve the later mentioned displacement measurement accuracy.

Each sampling point determined like this is arranged with a predetermined phase difference from a respective adjacent sampling point in both the hyperbola direction and the ellipse direction. This allows the phase intervals in the data to be equal when the data handled in the later mentioned displacement measurement, which simplifies the calculation procedure.

An example of a method of arranging the sampling points having an equal phase difference like this will now be shown.

The following Expression (12) represent coordinates $x_{ij}$, $y_{ij}$ of each point with respect to a hyperbola index i and an ellipse index j (i=0, ±1, ±2, . . . , j=1, 2, 3, . . . ).

[Math. 9]

$$\begin{pmatrix} x_{ij} \\ y_{ij} \end{pmatrix} \begin{pmatrix} \dfrac{\frac{1}{2}cTi\left(\frac{1}{2}cTj+f\right)}{f} \\ \dfrac{\sqrt{\left(\left(\frac{1}{2}cTj\right)^2+cTjf\right)\left(f^2-\left(\frac{1}{2}cTi\right)^2\right)}}{f} \end{pmatrix} \quad (12)$$

Here c denotes sound velocity, T denotes a sampling interval, and f denotes a distance from the center of the probe to the peak of apodization (described later).

The signal acquired in this state is based on the ellipse-hyperbola plane generated by converting coordinates from the x-y plane to the ellipse-hyperbola plane. FIG. 5 shows a concept of this coordinate change.

Figure 5A:
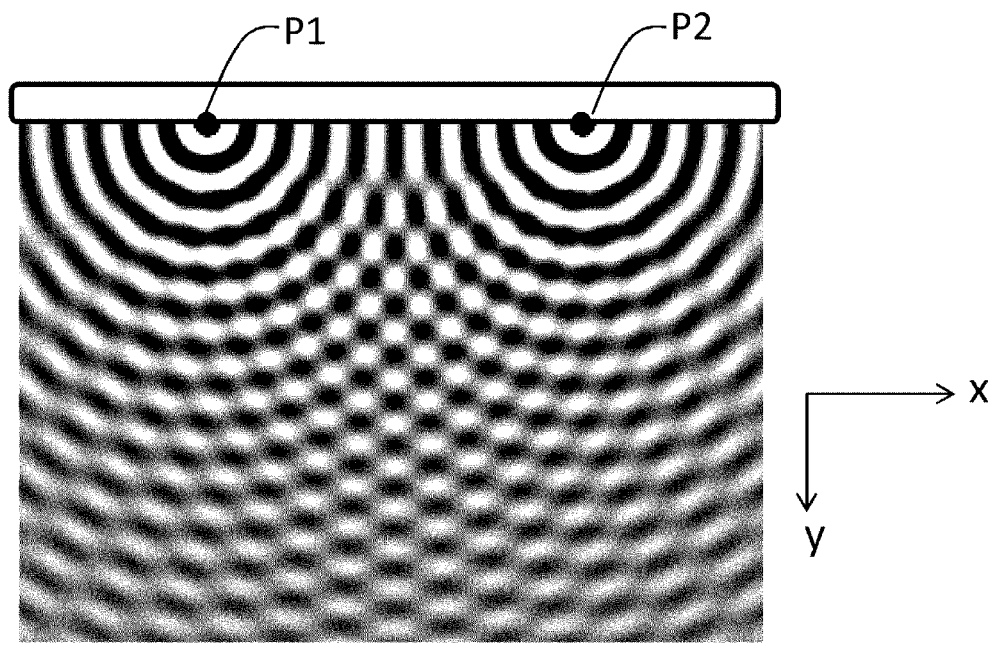
FIGS. 5A and 5B show modulation using a hyperbola and an ellipse.
Figure 5B:
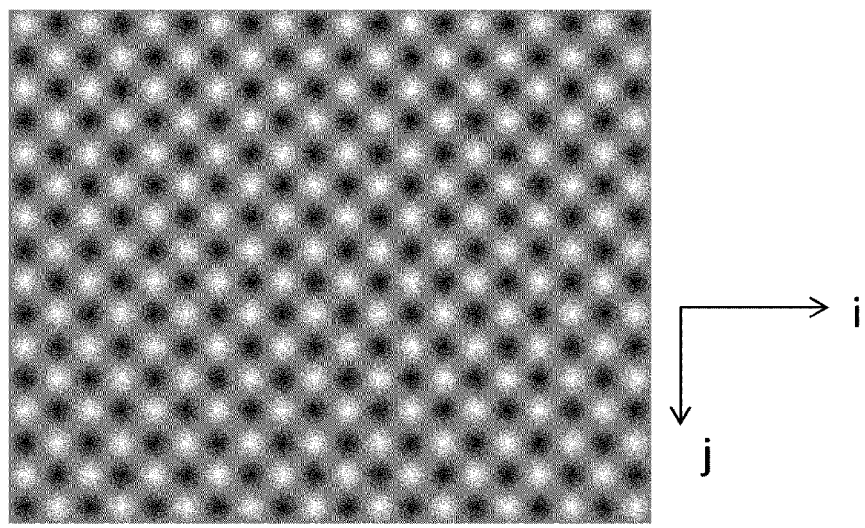

FIG. 5A shows a state when ultrasound waves are continuously generated from the peaks P1 and P2 of apodization, and these waves cause interference. In the x-y plane where this interference is occurring, the above mentioned data in the coordinates $x_{ij}$, $y_{ij}$ is acquired and plotted, with the hyperbola index i as the abscissa and the ellipse index j as the ordinate, then data with an equal phase interval is acquired, as shown in FIG. 5B. The orthogonally intersecting two axes (abscissa (hyperbola index axis) and ordinate (ellipse index axis)) are modulated independently from each other, so the processing scale of the displacement estimation can be controlled by performing displacement estimation after separating the data into wave components of each axis.

When the aperture synthesis processing is executed, two types of apodization are used, that is, normal apodization performed in a standard ultrasound apparatus, and modulation apodization for measuring displacement. Apodization here refers to a weight that is applied to a plurality of elements upon transmission and reception, and for normal apodization, Gaussian, Hamming and Hanning, for example, can be used.

Now the modulation apodization for measuring the displacement will be described.

Upon transmitting ultrasound waves using a plurality of elements, Fourier transform of the weights (apodization) applied to the plurality of elements used for the transmission has a sound pressure distribution in a direction perpendicular to the ultrasound wave transmitting/receiving direction near a focal point. To generate a sinusoid modulation in a direction perpendicular to the ultrasound transmitting/receiving direction near a focal point, on the other hand, apodization of an inverse Fourier transform of the modulation is applied.

For example, modulation is possible by using the modulation apodization of $w_t(x)$ for transmission, and $w_r(x)$ for reception. $w_t(x)$ and $w_r(x)$ are given by Expression (13) and Expression (14) respectively.

[Math. 10]

$$w_t(x) = \frac{1}{2}\left[\exp\left(\frac{x-x_0}{\sigma_0}\right)^2 + \exp\left(\frac{x+x_0}{\sigma_0}\right)^2\right] \quad (13)$$

$$w_r(x) = \frac{1}{2}\left[\exp\left(\frac{x-x_0}{\sigma_0}\right)^2 + \exp\left(\frac{x+x_0}{\sigma_0}\right)^2\right] \quad (14)$$

Here $x_0 = y\lambda f_x$, $\sigma_0 = (y\lambda\sqrt{2})/\sigma_x$, y is a depth to form a focal point, $\lambda$ is a wavelength of an ultrasound wave, $f_x$ is a frequency of modulation near the focal point, and $\sigma_x$ is FWHM (Full Width at Half Maximum) of a Gaussian envelope of a sin wave modulated near the focal point.

A method of using the modulation apodization is not limited to this. For example, modulation can be performed in the same way by virtually forming sub-apertures at two locations in an aperture formed by a plurality of elements used only for one of transmission and reception, and transmitting or receiving coherent ultrasound waves from the sub-apertures. In other words, the modulation apodization becomes possible by using a weight having two peaks.

The signal acquired by the normal apodization (step S404) is outputted to the image generation block 008 as a first aperture synthesis signal (step S405). The signal acquired by the modulation apodization (step S406) is outputted to the displacement calculation block 009 as the second aperture synthesis signal (step S407).

To perform aperture synthesis using the normal apodization, sampling points may be set on a straight line linearly extending from the probe aperture, rather than setting the sampling points to the intersections of the hyperbola group and ellipse group having two common focal points.

(Calculation of Displacement)

Operation in the displacement calculation block 009 will now be described.

A plurality of second aperture synthesis signals, which are the aperture synthesis processing result calculated using receive signals acquired at different time points, are inputted to the displacement calculation block 009.

Here a method of calculating displacement based on the plurality of second aperture synthesis signals, that is, aperture synthesis processing results acquired at different time points, will be described.

For example, a method for calculating displacement by independently determining an IQ signal for a hyperbola index axis and an ellipse index axis will be described.

When u denotes a position on the hyperbola index axis and v denotes a position on the ellipse index axis, the inputted second aperture synthesis signals can be modeled using the following Expression (15).

[Math. 11]

$$rf(u,v) = A(u,v)\cos(2\pi f_u + \phi_u)\cos(2\pi f_v + \phi_v) \quad (15)$$

A denotes an envelope curve of the second aperture synthesis signal, $f_u$ and $f_v$ denote modulation frequencies in the hyperbola index axis direction and the ellipse index axis direction respectively, and $\phi_u$ and $\phi_v$ denote phases in the hyperbola index axis position and the ellipse index axis direction respectively.

Here the IQ signals $I_u(u, v)$ and $Q_u(u, v)$ of the waves in the hyperbola index axis direction and the IQ signals $I_v(u, v)$ and $Q_v(u,v)$ of the waves in the ellipse index axis direction can be calculated using the following Expression (16) to Expression (19).

[Math. 12]

$$I_u(u,v) = (II^2(u,v) + IQ^2(u,v)) - (QI^2(u,v) + QQ^2(u,v)) \quad (16)$$

$$Q_u(u,v) = 2(II(u,v)QI(u,v) + IQ(u,v)QQ(u,v)) \quad (17)$$

$$I_v(u,v) = (II^2(u,v) + QI^2(u,v)) - (IQ^2(u,v) + QQ^2(u,v)) \quad (18)$$

$$Q_v(u,v) = 2(II(u,v)IQ(u,v) + QI(u,v)QQ(u,v)) \quad (19)$$

Here II (u, v), IQ (u, v), QI (u, v) and QQ (u,v) are given by the following Expression (20) to Expression (23).

[Math. 13]

$$II(u,v)=4LPF\{rf(u,v)\cos(2\pi f_u u)\cos(2\pi f_v v)\} \quad (20)$$

$$IQ(u,v)=4LPF\{rf(u,v)\cos(2\pi f_u u)\sin(-2\pi f_v v)\} \quad (21)$$

$$QI(u,v)=4LPF\{rf(u,v)\sin(-2\pi f_u u)\cos(2\pi f_v v)\} \quad (22)$$

$$QQ(u,v)=4LPF\{rf(u,v)\sin(-2\pi f_u u)\sin(-2\pi f_v v)\} \quad (23)$$

LPF refers to a "low pass filter" of which cut-off frequencies are $f_u$ and $f_v$.

In this case, the envelope curve A (u,v), phase $\phi_u$ in the hyperbola index axis direction, and phase $\phi_v$ in the ellipse index axis direction are determined using the following Expression (24) to Expression (26).

[Math. 14]

$$A(u,v) = \sqrt[4]{I_u^2(u,v) + Q_u^2(u,v)} \quad (24)$$

$$\phi_u = \frac{\tan^{-1}\{Q_u(u,v)/I_u(u,v)\}}{2} \quad (25)$$

$$\phi_v = \frac{\tan^{-1}\{Q_v(u,v)/I_v(u,v)\}}{2} \quad (26)$$

Phrases of the second aperture synthesis signals acquired at different timings are denoted with $\phi_{u1}$, $\phi_{u2}$, $\phi_{v1}$ and $\phi_{v2}$ respectively. In this case, the displacement in two direction, that is displacement $\delta_u$ in the hyperbola index axis direction and displacement $\delta_v$ in the ellipse index axis direction can be calculated using the following Expression (27) and Expression (28).

[Math. 15]

$$\delta_u = \frac{\phi_{u2} - \phi_{u1}}{2\pi} \lambda_u \quad (27)$$

$$\delta_v = \frac{\phi_{v2} - \phi_{v1}}{2\pi} \lambda_v \quad (28)$$

Here $\lambda_u$ and $\lambda_v$ are wavelengths in the hyperbola index axis direction and the ellipse index axis direction respectively.

In this way, the displacement distribution in the necessary observation range can be calculated. This way of calculating displacement using the IQ data of the second aperture synthesis signal becomes possible because sampled points are arranged with a constant phase difference in both the hyperbola direction and the ellipse direction, and contributes to reducing the calculation scale. Furthermore higher displacement estimation accuracy can be implemented, since the displacement calculating processing is performed on a signal having a high SN ratio based on a code string signal.

(Modification 1 of Displacement Calculation)

In the above example, a technique to use IQ signals separated into the hyperbola index axis direction and the ellipse index axis direction was described, but a technique to extract phase information and displacement information from a plurality of waveform signals may be used.

For example, the displacement can also be calculated using a following technique.

Envelope curves of the second aperture synthesis signals acquired at different timings are determined, and a general displacement ($\delta_u'$, $\delta_v'$) is estimated by the cross-correlation of these envelope curves. After correcting the general displacement, a phase difference ($\phi_u'$, $\phi_v'$) is calculated using complex correlation. Further, instantaneous frequencies ($f_u$, $f_v$) at a target position are estimated.

The displacement $\delta_u$ in the hyper bola index axis direction and the displacement $\delta_v$ in the ellipse index axis direction can be calculated using the following Expression (29) and Expression (30). Here c is a sound velocity.

[Math. 16]

$$\delta_u = \delta_u' + \frac{\phi_u'}{2\pi} \frac{c}{f_u} \quad (29)$$

$$\delta_v = \delta_v' + \frac{\phi_v'}{2\pi} \frac{c}{f_v} \quad (30)$$

According to this technique, an instantaneous frequency is estimated and the estimation result thereof is used, whereby the displacement can be stably determined even if the frequency changes due to a shift of the hyperbola group and the ellipse group in the observation area. Furthermore estimating the instantaneous frequency generates an effect of improving the accuracy.

According to this technique, displacement in the horizontal direction can be measured without using signals sampled at the intersections of the hyperbola group and the ellipse group, since the instantaneous frequency is estimated for each observation section. Even in this case, an effect of improving the SN ratio by the encoded transmission and reception can be implemented.

(Modification 2 of Displacement Calculation)

The displacement can also be calculated using the following technique.

The envelope curves of the second aperture synthesis signals acquired at different timings are determined, and a general displacement ($\delta_u'$, $\delta_v'$) is estimated by the cross-correlation of these envelope curves. Then an argument R ($\Delta u$, $\Delta v$: u, v) of a complex correlation is calculated by providing an arbitrary amount of deviation $\Delta u$ and $\Delta v$, assuming that the second aperture synthesis signals, after correcting the general displacement, are $s_1(u,v)$ and $s_2(u,v)$. This is given by Expression (31).

[Math. 17]

$$R(\Delta u, \Delta v: u, v) = \arg\left\{\iint_{\Omega(x,y)} s_2(\xi, \eta) s_1^*(\xi + \Delta u, \eta + \Delta v) d\xi d\eta\right\} \quad (31)$$

The argument R ($\Delta u$, $\Delta v$: u, v) of the complex correlation becomes 0 when the displacement ($\delta_u'+\Delta u$, $\delta_v'+\Delta v$) coincides with the true displacements. In concrete terms, approximating that the argument changes as a linear function, linear interpolation is performed with a plurality of ($\Delta u$, $\Delta v$) at which the argument R ($\Delta u$, $\Delta v$: u, v) is a value close to 0, and a likely displacement is calculated.

According to this technique, the displacement itself is estimated, hence the displacement can be stably determined even if the frequency is changed by the deviation of the hyperbola group and the ellipse group in the observation area, and an effect of improving the displacement estimation accuracy can be expected. Since the displacement itself is estimated for each observation location in this technique, the displacement in the horizontal direction can be measured without using signals sampled at the intersections of the hyperbola group and the ellipse group, and even in this case, an effect of improving the SN ratio of the encoded transmission and reception can be implemented.

(Calculation of Strain)

Now a technique to determine a strain distribution using the displacement data ($\delta_u$, $\delta_v$) will be described.

The displacement data is calculated as displacement vectors by performing coordinate transformation from the ellipse-hyperbola plane to the x-y plane. By differentiating the displacement vectors in the x direction and the y direction respectively, the strain distribution can be calculated. The same result can also be obtained by calculating the strain distribution in the ellipse-hyperbola plane first, then performing the coordinate transformation into the x-y plane.

Since differential processing is performed to calculate the strain distribution, noise with high spatial frequency may be generated. In order to reduce this noise, processing to improve visibility may be performed in the image processing block 010, such as applying a spatial low pass filter for the calculated strain distribution.

As described above, according to the present invention that uses the code string signal, a higher SN ratio can be implemented for a signal just like the case when transmission is performed for each element, that is suitable for the aperture synthesis method. Furthermore, an object information processing apparatus having higher displacement estimation accuracy can be implemented since the displacement is estimated using the signal having a high SN ratio.

Figure 7A:
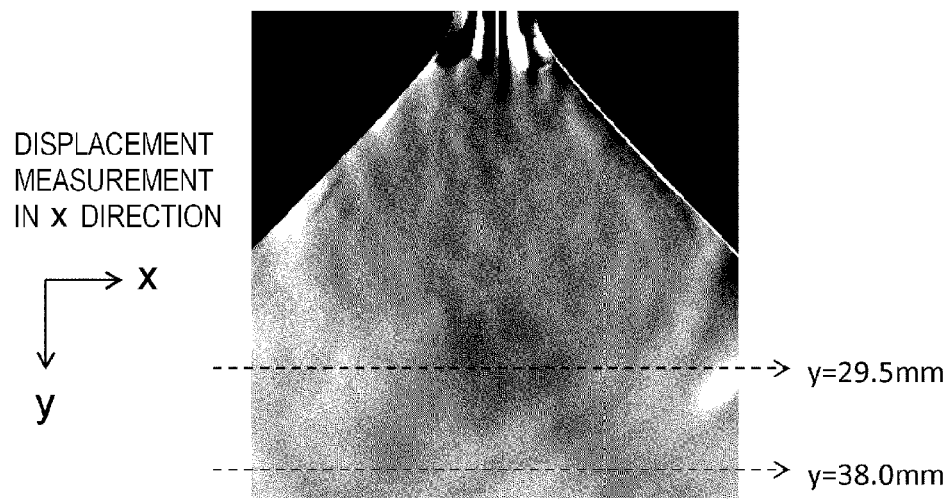
FIGS. 7A and 7B are diagrams depicting an example of a displacement calculation result.

FIG. 7A shows a strain distribution estimated using the present invention. An enclosed substance (area enclosed by dotted lines) of which diameter is 9 mm and of which hardness is higher than the peripheral area is set inside agar-agar, and about 0.5% compression is applied in the direction to the right in FIG. 7A, that is a direction perpendicular to the probe (contacting the upper part in FIG. 7A), which is not illustrated. The displacement before and after applying the compression is calculated according to the present invention, and the strain distribution in the horizontal direction is calculated. FIG. 7A shows the strain distribution in gray scale.

Figure 7B:
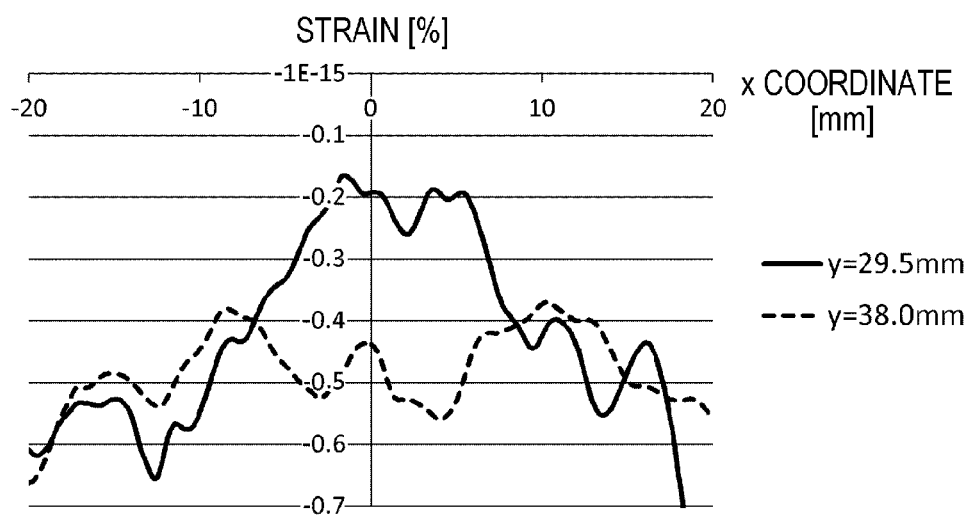

FIG. 7B is a result of plotting the strain distribution in the horizontal direction in two locations in FIG. 7A (on two straight lines, y=29.5 mm and 38.0 mm). The strain distribution in the horizontal direction on the straight line at y=29.5 mm is indicated by a solid line, and the strain distribution in the horizontal direction on the straight line at y=38.0 mm is indicated by a dotted line. The strain distribution in the horizontal direction on the straight line at y=38.0 mm, indicated by the dotted line, is constant approximately at −0.5%, that is, the measurement result reflects a state where the enclosed substance is compressed with about 0.5% compression in the horizontal direction. For the strain distribution in the horizontal direction on the straight line at y=29.5 mm, indicated by the solid line, an area in which strain is low (about −0.2%) exists approximately around the center, and the measurement result reflects the state that the enclosed substance is harder than the peripheral agar-agar.

<Embodiment 2>

Upon outputting the voltage waveform of which phase is changed according to the code string signal, the voltage waveform need not always have one wavelength for one code. In other words, the voltage waveform of which phase is changed may have a length of a plurality of wavelengths.

If a voltage waveform having a plurality of wavelengths is used like this, the SN ratio and displacement estimation accuracy further improve, compared with the case of using the voltage waveform having one wavelength.

However, as the length of the voltage waveform increases, the spatial resolution to estimate displacement decreases, therefore it is desirable to keep the length of the voltage waveform to be a length less than or equal to the spatial resolution determined by the above mentioned spatial low pass filter.

<Embodiment 3>

Each value of the code string signal may be applied to a plurality of elements, instead of one element at a time.

An example of applying each value of the code string signal to a plurality of elements will be described with a reference to FIG. 6. The code string signal used here is the same as that described in the above example.

Figure 6:
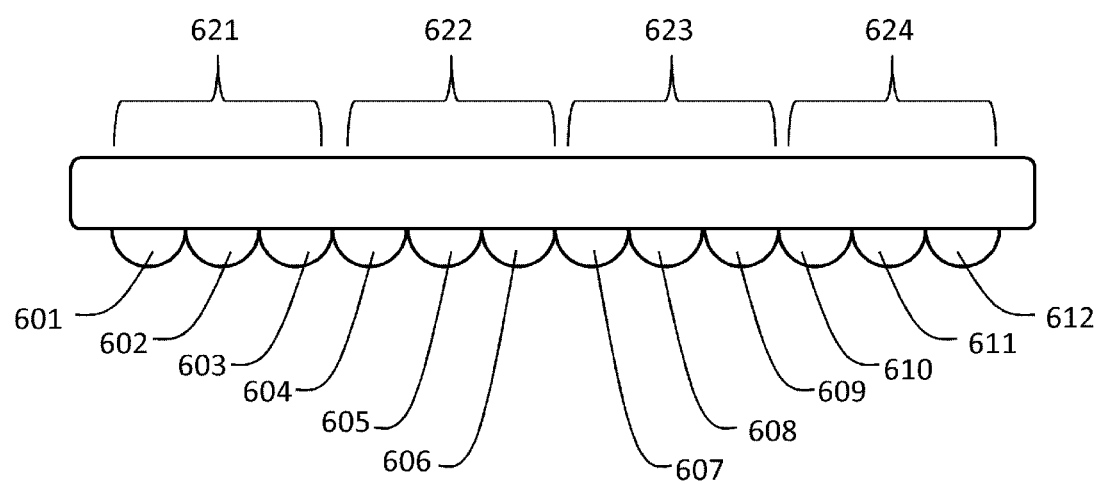
FIG. 6 shows a state when the code string signal is applied to a plurality of elements.

In this case, the elements of the transmitting and receiving unit are grouped as shown in FIG. 6. An element 601 to an element 603 constitute an element group A (621), an element 604 to an element 606 constitute an element group B (622), an element 607 to an element 609 constitute an element group C (623), and an element 610 to an element 612 constitute an element group D (624).

The code string signal transmitted from the code control block 002 is inputted to the transmitting circuit system 005. In the transmitting circuit system 005, the voltage waveform is transmitted to twelve elements, that is the element 601 to the element 612.

First a voltage waveform in a same phase (this phase is assumed to be 0°, for example) is transmitted to the element group A, element group B, element group C and element group D using (1, 1, 1, 1), which are arranged in the first column of the code string signal.

Then a voltage waveform is transmitted to the element group A in phase 0°, to the element group B in phase 180° to the element group C in phase 0°, and to the element group D in phase 180° according to (1, −1, 1, −1), which are arranged in the second column of the code string signal.

In this way, each value of the code signal is applied to a plurality of elements (three elements in this case), and the ultrasound wave is transmitted to the object accordingly. Then the ultrasound wave reflected inside the object is received and decoded. The decoded result is different from the signal in the case of transmitting each value of the code string signal to one element at a time, a transmitted signal is separated respectively in the element group A, the element group B, the element group C and the element group D.

Description on the step of performing the aperture synthesis processing using these decoded signals and subsequent steps, which is the same as the content already described above, is omitted here.

If transmission is performed using a same code string signal for a plurality of elements, the number of times of transmission/reception can be less than the number of elements used for the transmission/reception, and data can be acquired at higher speed. This allows to stably and accurately measure the displacement and strain of which change is fast.

A plurality of elements (e.g. element group A), to which each value of the code string signal is applied, can form a more spherical or columnar wavefront by virtually setting a wave source inside the transmitting/receiving unit (probe) or inside the object. Thereby compared with the case of simultaneously transmitting voltage waveforms to the plurality of elements, spatial resolution by the aperture synthesis method can be further improved, and the accuracy of the displacement measurement can be further improved.

Modifications 1 and 2 of the displacement measurement described in Embodiment 1 are preferable examples in terms of controlling the measurement errors in the displacement measurement and improving the signal level as mentioned above. However in these examples, the encoded pulse need not always be used in terms of controlling the measurement error. In other words, the effect of controlling the measurement error can be exhibited even if the transmitting pulse is not an encoded pulse.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-243483, filed on Nov. 7, 2011, which is hereby incorporated by reference herein in its entirety.

The invention claimed is:

1. An object information acquiring apparatus that transmits an elastic wave to an object and receives a reflected wave, which is the transmitted elastic wave reflected in the object, so as to acquire information on the object, the apparatus comprising:
    a transmitting and receiving unit having a plurality of elements which can perform conversion between an elastic wave and an electric signal, with these elements being arranged at least in one direction;
    an element controlling unit that inputs an electric signal to the elements and causes the elements to transmit an elastic wave to the object; and
    a detecting unit that detects the reflected wave, which is the transmitted elastic wave reflected in the object and received by the elements, wherein
    the electric signal which the element controlling unit inputs to one element of the elements is an encoded pulse signal encoded corresponding to that one element among the plurality of elements, and
    the detecting unit decodes the reflected wave and executes an aperture synthesis processing at different time points, by setting as axes a direction along a hyperbola of which focal points are two locations in the one direction in which the plurality of elements are arranged and a direction along an ellipse of which focal points are these two locations, and synthesizing the decoded reflected wave in the intersections of these axes or in locations corresponding to the intersections, and acquires displacement values of the object at least in two directions based on the aperture synthesis processing results at the different time points.

2. The object information acquiring apparatus according to claim 1, wherein the displacement value is acquired based on an instantaneous frequency estimation result in the aperture synthesis processing result in the intersections or the locations corresponding to the intersections.

3. The object information acquiring apparatus according to claim 1, wherein the encoded pulse signal is encoded for each group of a plurality of N elements, where N is a natural number.

4. An object information acquiring apparatus that transmits an elastic wave to an object and receives a reflected wave, which is the transmitted elastic wave reflected in the object, so as to acquire information on the object, the apparatus comprising:
    a transmitting and receiving unit in which a plurality of elements, which can perform conversion between an elastic wave and an electric signal, are arranged;
    an element controlling unit that inputs an electric signal to the elements and causes the elements to transmit an elastic wave to the object; and
    a detecting unit that detects the reflected wave, which is the transmitted elastic wave reflected in the object and received by the elements, wherein
    the electric signal which the element controlling unit inputs to one element of the elements is an encoded pulse signal encoded corresponding to that one element among the plurality of elements,
    the detecting unit decodes the reflected wave and executes an aperture synthesis processing for synthesizing the decoded reflected waves at different time points, and acquires displacement values of the object at least in two directions based on aperture synthesis processing results at the different time points, and
    wherein the displacement value is acquired based on an instantaneous frequency estimation result in the aperture synthesis processing result in intersections of two axes or the locations corresponding to the intersections.

5. The object information acquiring apparatus according to claim 4, wherein the encoded pulse signal is encoded for each group of a plurality of N elements, where N is a natural number.

6. An object information acquiring apparatus comprising:
    a detecting unit in which a plurality of elements which can perform conversion between an elastic wave and an electric signal are arranged in one direction,
    wherein the detecting unit
        decodes a reflected wave which has been transmitted from the plurality of elements and reflected by an object, in response to an input of an encoded pulse signal encoded corresponding to one element among the plurality of elements into a transmitting and receiving unit,
        executes an aperture synthesis processing at different time points, on intersections of axes or in positions corresponding to the intersections, the axes including an axis in a direction along a hyperbola of which focal points are two locations in the one direction in which the plurality of elements are arranged and an axis in a direction along an ellipse of which focal points are these two locations, and
        acquires displacement values of the object in at least two directions based on aperture synthesis processing results at the different time point, and
    wherein the displacement value is acquired based on an instantaneous frequency estimation result in the aperture synthesis processing result in the intersections or the locations corresponding to the intersections.

* * * * *